United States Patent
Thomas et al.

(10) Patent No.: US 10,166,360 B2
(45) Date of Patent: Jan. 1, 2019

(54) SYSTEM AND METHOD FOR CONTROLLING FLOW DURING EXHALATION IN A RESPIRATORY SUPPORT SYSTEM

(71) Applicant: KONINKLIJKE PHILIPS N.V., Eindhoven (NL)

(72) Inventors: Charles Thomas, Monroeville, PA (US); Manuel Laura Lapoint, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 401 days.

(21) Appl. No.: 14/391,773

(22) PCT Filed: Apr. 23, 2013

(86) PCT No.: PCT/IB2013/053194
§ 371 (c)(1),
(2) Date: Oct. 10, 2014

(87) PCT Pub. No.: WO2013/164733
PCT Pub. Date: Nov. 7, 2013

(65) Prior Publication Data
US 2015/0136135 A1    May 21, 2015

Related U.S. Application Data

(60) Provisional application No. 61/640,895, filed on May 1, 2012.

(51) Int. Cl.
*A61M 16/20*  (2006.01)
*A61M 16/00*  (2006.01)
(Continued)

(52) U.S. Cl.
CPC ...... *A61M 16/205* (2014.02); *A61M 16/0003* (2014.02); *A61M 16/0051* (2013.01);
(Continued)

(58) Field of Classification Search
CPC .......... A61M 16/205; A61M 16/0003; A61M 16/0069; A61M 16/161; A61M 16/206;
(Continued)

(56) References Cited

U.S. PATENT DOCUMENTS 5,954,051 A  *  9/1999  Heinonen ............. A61M 16/00
                                                  128/204.21
6,360,741 B2 *  3/2002  Truschel ........... A61M 16/0051
                                                  128/202.22
(Continued)

FOREIGN PATENT DOCUMENTS

WO         0045882 A1   8/2000
WO     2011145014 A1  11/2011
WO     20120127415 A1  9/2012

*Primary Examiner* — Gregory Anderson
*Assistant Examiner* — Jonathan Paciorek
(74) *Attorney, Agent, or Firm* — Charles Kosinski (57) ABSTRACT

The present disclosure pertains to an exhalation valve system (10) configured to control gas flow during exhalation of a subject (12). In some embodiments, the system comprises one or more of a pressure generator (14), a subject interface (16), one or more sensors (18), one or more processors (20), electronic storage (22), user interface (23), and/or other components. The system is configured to adjust a rebreathing level of the subject based on detected occurrences of disordered breathing events. By rebreathing exhaled air (and/or other breathable gas) a subject may minimize and/or prevent central sleep apneas. The system monitors the breathing of the subject to detect occurrences of respiratory events related to central sleep apnea. The system monitors accumulated retrograde breathing and adjusts the volume of exhaled rebreathing and/or other system settings affecting (Continued)

the subject's breathing. Through these adjustments, the system may prevent and/or reduce respiratory events related to central sleep apnea.

21 Claims, 6 Drawing Sheets (51) Int. Cl.
*A61M 16/16* (2006.01)
*A61M 16/06* (2006.01)

(52) U.S. Cl.
CPC ........ *A61M 16/0069* (2014.02); *A61M 16/06* (2013.01); *A61M 16/161* (2014.02); *A61M 16/20* (2013.01); *A61M 16/206* (2014.02); A61M 16/0009 (2014.02); A61M 16/0045 (2013.01); A61M 16/0075 (2013.01); A61M 2016/003 (2013.01); A61M 2016/0027 (2013.01); A61M 2016/0033 (2013.01); A61M 2205/18 (2013.01); A61M 2205/3317 (2013.01); A61M 2205/3334 (2013.01); A61M 2205/3365 (2013.01); A61M 2205/3368 (2013.01); A61M 2205/3592 (2013.01); A61M 2205/502 (2013.01); A61M 2205/505 (2013.01); A61M 2230/005 (2013.01); A61M 2230/40 (2013.01); A61M 2230/42 (2013.01); A61M 2230/43 (2013.01)

(58) Field of Classification Search
CPC .. A61M 16/0051; A61M 16/06; A61M 16/20; A61M 16/0009; A61M 16/0045; A61M 2016/0027; A61M 2016/003; A61M 2205/18; A61M 2205/3317; A61M 2205/3334; A61M 2205/336; A61M 2205/3368; A61M 2205/3592; A61M 2205/502; A61M 2230/005; A61M 2230/40; A61M 2230/42; A61M 2230/43
See application file for complete search history.

(56) References Cited

U.S. PATENT DOCUMENTS

| | | | |
|---|---|---|---|
| 7,810,497 B2 * | 10/2010 | Pittman | A61M 16/0051 128/204.18 |
| 2004/0144383 A1 * | 7/2004 | Thomas | A61M 16/0045 128/204.18 |
| 2005/0066964 A1 * | 3/2005 | Bathe | A61M 16/08 128/200.14 |
| 2007/0221224 A1 * | 9/2007 | Pittman | A61M 16/0069 128/204.22 |
| 2008/0302364 A1 | 12/2008 | Garde et al. | |
| 2010/0024824 A1 * | 2/2010 | Chalvignac | A61M 16/00 128/205.24 |

* cited by examiner

SYSTEM AND METHOD FOR CONTROLLING FLOW DURING EXHALATION IN A RESPIRATORY SUPPORT SYSTEM

CROSS-REFERENCE TO PRIOR APPLICATIONS

This application is the U.S. National Phase application under 35 U.S.C. § 371 of International Application No. PCST/IB2013/053194, filed on Apr. 23, 2013, which claims the benefit of U.S. Provisional Patent Application No. 61/640,895, filed on May 1, 2012. These applications are hereby incorporated by reference herein.

The present disclosure pertains to an exhalation valve system configured to control gas flow during exhalation of a subject.

Central sleep apnea occurs when the brain temporarily stops sending signals to the muscles that control breathing. Without a signal, the muscles do not operate to inflate the lungs with air as they normally would. Various systems to treat central sleep apnea are known. They include positive airway pressure systems, adaptive servo ventilation systems, and added dead space systems. Typical added dead space systems operate to treat central sleep apnea by holding exhaled gas ($CO_2$ rich) in a dead space that is added to and attached to a patient respiratory circuit.

Accordingly, one or more aspects of the present disclosure relate to an exhalation valve system configured to control gas flow during exhalation of a subject. The system comprises a pressure generator, a subject interface, one or more sensors, and one or more processors. The pressure generator is configured to generate a pressurized flow of breathable gas for delivery to an airway of the subject. The subject interface is configured to communicate the pressurized flow of breathable gas to the airway of the subject. The subject interface comprises an exhalation port and a valve. The exhalation port is configured to place the interior of the subject interface in communication with the exterior of the subject interface. The valve is positioned between the pressure generator and the airway and is configured to selectively control flow through the exhalation port. The valve operates in a first mode in which the exhalation port is opened to permit gas flow from the airway of the subject during exhalation, and a second mode in which flow through the exhalation port is restricted with respect to the flow in the first mode. The one or more sensors are configured to generate output signals conveying information related to one or more gas parameters of the pressurized flow of breathable gas. The processor is configured to execute computer program modules. The computer program modules comprise a disordered breathing event detection module and a control module. The disordered breathing event detection module is configured to detect the onset of a disordered breathing event, wherein the onset of the disordered breathing event is determined based on the output signals of the sensors. The control module is configured to control operation of the valve between the first mode and the second mode based on detections by the disordered breathing event detection module.

Yet another aspect of the present disclosure relates to a method of controlling gas flow during exhalation of a subject. The method is performed by a system that includes a pressure generator, a subject interface, one or more sensors, and one or more processors. The method comprises generating, with the pressure generator, a pressurized flow of breathable gas for delivery to an airway of the subject; delivering the pressurized flow of breathable gas to the airway of the subject with the subject interface; providing fluid communication between the interior of the subject interface and the exterior of the subject interface through an exhalation port, the exhalation port positioned between the pressure generator and the airway; generating, with the one or more sensors, output signals conveying information related to one or more gas parameters of the pressurized flow of breathable gas; detecting, with the one or more processors, the onset of a disordered breathing event, wherein the onset of the disordered breathing event is detected based on the output signals; and controlling, by the one or more processors, flow through the exhalation port with a valve, wherein such control includes causing the valve to switch between a first mode in which the exhalation port is opened to permit gas flow from the airway of the subject during exhalation, and a second mode in which flow through the exhalation port is restricted with respect to the flow in the first mode, wherein such control comprises switching operation of the valve between the first mode and the second mode based on detections of the onset of disordered breathing events.

Still another aspect of present disclosure relates to an exhalation valve system configured to control gas flow during exhalation of a subject. The system comprises means for generating a pressurized flow of breathable gas for delivery to an airway of the subject; means for delivering the pressurized flow of breathable gas to the airway of the subject; means for providing fluid communication between the interior of the means for communicating the pressurized flow of breathable gas to the airway of the subject and the exterior of the means for communicating the pressurized flow of breathable gas to the airway of the subject; means for generating output signals conveying information related to one or more gas parameters of the pressurized flow of breathable gas; means for detecting the onset of a disordered breathing event, wherein the onset of the disordered breathing event is detected based on the output signals; and means for controlling flow through the means for interior/exterior communication with a means for selectively controlling flow, wherein such control includes causing the means for selectively controlling flow to switch between a first mode in which the means for interior/exterior communication is opened to permit gas flow from the airway of the subject during exhalation, and a second mode in which flow through the means for interior/exterior communication is restricted with respect to the flow in the first mode, wherein such control comprises switching operation of the means for selectively controlling flow between the first mode and the second mode based on detections of the onset of disordered breathing events.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
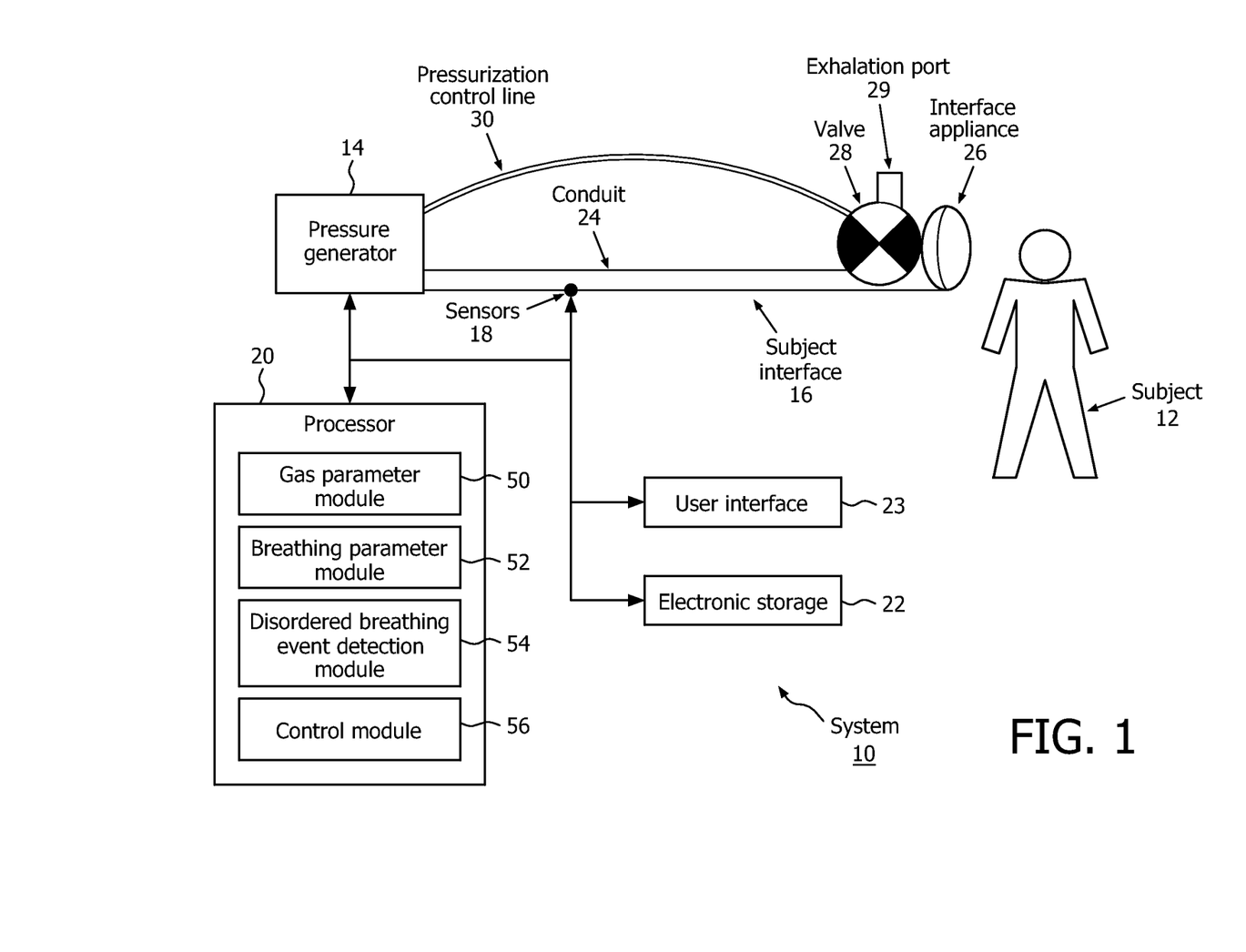
FIG. 1 is a schematic of an exhalation valve system configured to control gas flow during exhalation of a subject.

FIG. 1 schematically illustrates a system 10 configured to control gas flow during exhalation of a subject 12. In some embodiments, system 10 comprises one or more of a pressure generator 14, a subject interface 16, one or more sensors 18, one or more processors 20, electronic storage 22, user interface 23, and/or other components. System 10 is configured to adjust a rebreathing level of subject 12 based on detected occurrences of disordered breathing events. By rebreathing exhaled air (and/or other breathable gas) a subject may minimize and/or prevent central sleep apneas. The rebreathing level, or volume of rebreathed air, is also referred to as the retrograde volume. System 10 is configured to minimize the fixed dead space in the system. System 10 monitors the breathing of subject 12, as characterized by breathing parameters, to detect occurrences of respiratory events related to central sleep apnea. System 10 monitors accumulated retrograde breathing and adjusts the volume of exhaled rebreathing and/or other system settings affecting the subject's breathing. Through these adjustments, system 10 may prevent and/or reduce respiratory events related to central sleep apnea.

Pressure generator 14 is configured to provide a pressurized flow of breathable gas for delivery to the airway of subject 12. Pressure generator 14 is configured to deliver the pressurized flow of gas via subject interface 16, and/or other devices. Pressure generator 14 receives a flow of gas from a gas source, such as the ambient atmosphere, and elevates the pressure of that gas for delivery to subject 12.

Pressure generator 14 is configured such that one or more gas parameters of the pressurized flow of breathable gas are controlled in accordance with a therapy regime. The one or more gas parameters may include, for example, one or more of flow rate, pressure, volume, retrograde volume, accumulated retrograde volume, humidity, velocity, acceleration, and/or other parameters. In some embodiments, pressure generator 14 is a ventilator and/or positive airway pressure device. Pressure generator 14 is any device, such as, for example, a pump, blower, piston, or bellows, that is capable of elevating the pressure of the received gas for delivery to a patient. The present disclosure contemplates controlling the operating speed of the blower, for example, either alone or in combination with subject interface 16, and/or other devices, to control the pressure and/or flow rate of gas provided to subject 12. The present disclosure contemplates that gas other than ambient atmospheric air may be introduced into system 10 for delivery to the patient. In some embodiments system 10 is configured to provide types of therapy other than ventilation and/or positive airway pressure support, including types of therapy where subject 12 performs inspiration and/or expiration of his own accord, and/or where pressure generator 14 provides negative pressure.

Subject interface 16 is configured to interface with the airway of subject 12. Subject interface 16 is configured to provide fluid communication between pressure generator 14 and the airway of subject 12. As such, subject interface 16 comprises a conduit 24, an interface appliance 26, a valve 28, an exhalation port 29, and/or other components. Conduit 24 is configured to form a flow path through which the pressurized flow of breathable gas is communicated between pressure generator 14 and interface appliance 26. Conduit 24 may be a flexible length of hose, or other conduit, that places interface appliance 26 in fluid communication with pressure generator 14. Conduit 24 conveys gas (e.g., air) to and/or from interface appliance 26, and interface appliance 26 places conduit 24 in communication with the airway of subject 12. In some embodiments, interface appliance 26 is non-invasive. As such, interface appliance 26 non-invasively engages subject 12. Non-invasive engagement includes removably engaging an area (or areas) surrounding one or more external orifices of the airway of subject 12 (e.g., nostrils and/or mouth) to communicate gas between the airway of subject 12 and subject interface 16. Some examples of non-invasive interface appliance 26 may include, for example, a blow tube, a nasal cannula, a nasal mask, a nasal/oral mask, a full face mask, a total face mask, or other interface appliances that communicate a flow of gas with an airway of a subject.

In some embodiments, valve 28 is positioned between pressure generator 14 and the airway of subject 12, at the exhalation port 29 in subject interface 16 (e.g., in interface appliance 26). This may reduce the form factor of subject interface 16 with respect to conventional embodiments in which a separate limb or compartment of subject interface 16 is used to provide dead space for rebreathing. The position of valve 28 may facilitate retrofitting of valve 28 into embodiments of subject interface 16 and/or interface appliance 26 that were not previously configured for rebreathing. For example, valve 28 may be configured for installation into an exhaust port of a conventional mask for use in positive airway pressure therapy, valve 28 may be included in a circuit insert (not show) installed between conduit 25 and interface appliance 26, and/or may facilitate retrofitting subject interface 16 for rebreathing therapy in other ways.

Valve 28 is configured to selectively control flow through exhalation port 29. Valve 28 is configured to operate in a first mode, a second mode, and/or other modes. Valve 28 operates in a first mode in which exhalation port 29 is opened to permit gas flow from the airway of subject 12 during exhalation. Valve 28 operates in a second mode in which flow through exhalation port 29 is restricted with respect to the flow in the first mode. In some embodiments, gas flow is restricted such that during exhalation substantially no gas is communicated from the airway of the subject through exhalation port 29. In some embodiments, gas flow is restricted such that a decreased (but non-zero) amount of gas continues to flow through exhalation port 29. In some embodiments, valve 28 may be located on interface appliance 26, on conduit 24, at the junction between interface appliance 26 and conduit 24, and/or at other locations.

In some embodiments, valve 28 is coupled to a first end of a pressurization control line 30. A second end of pressurization control line 30 is coupled to pressure generator 14 separately from subject interface 16. In some embodiments, the second end of pressurization control line 30 may be coupled to a pressure source other than pressure generator 14. Pressurization control line 30 may be a flexible length of hose, or other conduit, that places valve 28 in fluid communication with pressure generator 14. Pressure control line 30 is configured to convey a control flow of gas (e.g., air) to valve 28. In some embodiments, the control flow of gas delivered to pressurization control line 30 is separate from the pressurized flow of breathable gas delivered to conduit 24. In some embodiments, the control flow of gas generated by pressure generator 14 is controlled by one or more valves within pressure generator 14, processor 20, and/or other components of system 10. Valve 28 is configured to receive the control flow of gas from pressure generator 14 via pressurization control line 30. Valve 28 is configured to operate in the first mode and the second mode with the flow of gas generated by pressure generator 14. Responsive to changes in the pressure of the control flow of gas, valve 28 is configured to switch between the first mode and the second mode. In some embodiments, valve 28 may comprise one or more valves in series and/or in parallel. In some embodiments, valve 28 functions at pressure levels of 1 cm $H_2O$ and above. In some embodiments, valve 28 functions at pressure levels of 2 cm $H_2O$ and above. In some embodiments, valve 28 functions at pressure levels of 4 cm $H_2O$ and above.

Sensors 18 are configured to generate output signals conveying information related to one or more gas parameters of the gas within subject interface 16. The one or more gas parameters comprise flow rate, volume, pressure, temperature, humidity, velocity, and/or other gas parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. By way of a non-limiting example, one or more of sensors 18 may generate an output based on an operating parameter of the pressure generator 14 (e.g., a motor current, voltage, rotational velocity, and/or other operating parameters), and/or other sensors. By way of a second non-limiting example, sensors 18 may generate output signals conveying information related to a respiratory effort of subject 12. This includes one or more of a thoracic respiratory effort, an abdominal respiratory effort, and/or other parameters indicating respiratory effort. Although sensors 18 are illustrated at a single location within (or in communication with) conduit 24 between valve 28 and pressure generator 14, this is not intended to be limiting. Sensors 18 may include sensors disposed in a plurality of locations, such as for example, within pressure generator 14, within (or in communication with) interface appliance 26, attached to subject 12, and/or other locations.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 includes a plurality of processing units. These processing units may be physically located within the same device, or processor 20 may represent processing functionality of a plurality of devices operating in coordination.

As shown in FIG. 1, processor 20 may be configured to execute one or more computer program modules. The one or more computer program modules comprise one or more of a gas parameter module 50, a breathing parameter module 52, a disordered breathing event detection module 54, a control module 56, and/or other modules. Processor 20 may be configured to execute modules 50, 52, 54, and/or 56 by software; hardware; firmware; some combination of software, hardware, and/or firmware; and/or other mechanisms for configuring processing capabilities on processor 20.

It should be appreciated that although modules 50, 52, 54 and 56 are illustrated in FIG. 1 as being co-located within a single processing unit, in implementations in which processor 20 includes multiple processing units, one or more of modules 50, 52, 54, and/or 56 may be located remotely from the other modules. The description of the functionality provided by the different modules 50, 52, 54, and/or 56 described below is for illustrative purposes, and is not intended to be limiting, as any of modules 50, 52, 54, and/or 56 may provide more or less functionality than is described. For example, one or more of modules 50, 52, 54, and/or 56 may be eliminated, and some or all of its functionality may be provided by other ones of modules 50, 52, 54, and/or 56. As another example, processor 20 may be configured to execute one or more additional modules that may perform some or all of the functionality attributed below to one of modules 50, 52, 54, and/or 56.

Gas parameter module 50 is configured to determine one or more gas parameters of the pressurized flow of breathable gas. Gas parameter module 50 is configured to determine the one or more gas parameters based on the output signals of sensors 18. The one or more gas parameters of the pressurized flow of breathable gas may comprise, for example, one or more of a flow rate, a volume, a pressure, humidity, temperature, acceleration, velocity, and/or other gas parameters. The information determined by gas parameter module 50 may be used for controlling pressure generator 14, determining breathing parameters of subject 12, and/or other uses.

Breathing parameter module 52 is configured to determine one or more breathing parameters of subject 12. The one or more breathing parameters are determined based on the one or more output signals generated by sensors 18, gas parameters determined by gas parameter module 52, and/or other information. The breathing parameters may indicate a respiratory effort of subject 12. This includes one or more of a thoracic respiratory effort, an abdominal respiratory effort, and/or other parameters indicating respiratory effort. The one or more breathing parameters may include, for example, a tidal volume, a composition, a timing (e.g., beginning and/or end of inhalation, beginning and/or end of exhalation, etc.), a duration (e.g., of inhalation, of exhalation, of a single breathing cycle, etc.), a breath rate, a respiration frequency, retrograde volume, accumulated retrograde volume, leak volume, and/or other parameters.

In some embodiments, breathing parameter module 52 determines the one or more breathing parameters based on previous respiration by subject 12. By way of a non-limiting example, breathing parameter module 52 may determine at least one breathing parameter for each exhalation in a series of consecutive exhalations. The at least one determined breathing parameter may include, for instance, retrograde volume, and/or other breathing parameters. By way of another non-limiting example, breathing parameter module 52 may determine at least one breathing parameter for a series of consecutive exhalations in addition to the breathing parameter determined for each individual exhalation. For example, breathing parameter module 52 may determine accumulated retrograde volume for a series of consecutive inhalations.

Disordered breathing event detection module 54 is configured to detect onset and/or occurrence of a disordered breathing event. Module 54 is configured to detect onset and/or occurrence of a disordered breathing event based on output signals from sensors 18, parameters determined by gas parameter module 50, parameters determined by breathing parameter module 52, and/or other information. In some embodiments, the disordered breathing event detected by module 54 may be related to central sleep apnea. In some embodiments, disordered breathing event detection module 54 may detect onset and/or occurrence of a disordered breathing event related to disordered breathing other than central sleep apnea. For example, module 54 may detect occurrences of Cheyne-Stokes respiration, obstructive sleep apneas, hypopneas, snoring, hyperventilation, and/or other disordered breathing.

Disordered breathing event detection module 54 is configured to detect a disordered breathing event during normal breathing of subject 12 through subject interface 16. This breathing occurs while valve 18 operates in the first mode so that subject 12 can inhale and exhale freely through subject interface 16. In some embodiments, the information indicating a disordered breathing event comprises one or more gas parameters (e.g. pressure, flow rate, and/or other gas parameters), one or more breathing parameters (e.g., a tidal volume, a composition, a timing, a duration, a breath rate, peak flow, airway pressure, and/or other breathing parameters), and/or other information. A disordered breathing event may comprise, for example, output signals and/or parameters that indicate lack (or significantly reduced level) of respiratory effort (e.g., thoracic respiratory effort and/or abdominal respiratory effort), a reduction in tidal volume, and/or changes in other output signals and/or parameters. In some embodiments, a disordered breathing event may be determined based on previous respiration by subject 12.

In some embodiments, disordered breathing event detection module 54 is configured to detect a disordered breathing event based on one or more gas parameters, one or more breathing parameters, and/or one or more other parameters breaching a threshold level (e.g., pressure and/or flow rate breaching threshold(s)). The threshold levels may be configurable to a user (e.g., subject 12, a doctor, a caregiver, a researcher, and/or other users), predefined at manufacture, determined based on previous respiration by subject 12, and/or determined in other manners.

Control module 56 is configured to control operation of valve 28 between the first mode and the second mode. Control module 56 is configured to control valve 28 based on detections by disordered breathing event detection module 54, information related to the output signals of sensors 18, a retrograde volume rebreathing algorithm, and/or other information. Based on detection of a disordered breathing event (and/or detection of the onset of a disordered breathing event) by disordered breathing event detection module 54, control module 56 is configured to cause valve 28 to operate in the second mode wherein flow through exhalation port 29 is restricted. Restricted flow through exhalation port 29 may adjust a rebreathing level (volume of rebreathed gas) of subject 12 by holding previously breathed gas in subject interface 16 until subject 12 inhales again, at which time subject 12 is forced to rebreath at least some of the previously breathed gas held in subject interface 16. Control module 56 may control the retrograde volume (volume of rebreathed gas) and/or the accumulated retrograde volume by controlling the amount of exhaled gas that flows through exhalation port 29 via valve 28. Control module 56 controls the amount of exhaled gas that flows through exhalation port 29 by varying the pressure of the control flow of gas delivered to valve 28 to open and/or close valve 28.

Control module 56 may control the retrograde volume based on an algorithm. The algorithm may be determined at manufacture, determined by programming the algorithm into processor 20, determined based on information entered by a user (e.g., a doctor, subject 12, etc.) via user interface 23, determined based the one or more output signals generated by one or more sensors 18, determined based on previous respiration by the subject, and/or determined by another method.

In some embodiments, control module 56 is configured to control pressure generator 14 and/or other devices to generate the flow of gas in accordance with a ventilator regime, a positive airway pressure therapy regime, a rebreathing therapy regime, and/or other therapy regimes. By way of non-limiting example, control module 56 may control pressure generator 14 such that the pressure support provided to subject 12 via the flow of gas comprises non-invasive ventilation, positive airway pressure support, continuous positive airway pressure support, bi-level support, BiPAP®, and/or other types of pressure support therapy.

In some embodiments, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 23, and/or other information that enables system 10 to function properly. Electronic storage 22 may be (in whole or in part) a separate component within system 10, or electronic storage 22 may be provided (in whole or in part) integrally with one or more other components of system 10 (e.g., pressure generator 14, processor 20, etc.).

User interface 23 is configured to provide an interface between system 10 and subject 12 through which subject 12 provides information to and receives information from system 10. This enables data, results, and/or instructions and any other communicable items, collectively referred to as "information," to be communicated between subject 12 and one or more of subject interface 16, processor 20, and/or other components of system 10. Examples of interface devices suitable for inclusion in user interface 23 include a keypad, buttons, switches, a keyboard, knobs, levers, a display screen, a touch screen, speakers, a microphone, an indicator light, an audible alarm, a printer, a tactile feedback device, a gesture recognition device, and/or other interface devices. In some embodiments, user interface 23 includes a plurality of separate interfaces. It is to be understood that other communication techniques, either hard-wired or wireless, are also contemplated by the present disclosure as user interface 23. Other exemplary input devices and techniques adapted for use with system 10 as user interface 23 include, but are not limited to, an RS-232 port, RF link, an IR link, modem (telephone, cable or other). In short, any technique for communicating information with system 10 is contemplated by the present disclosure as user interface 23.

Figure 2:
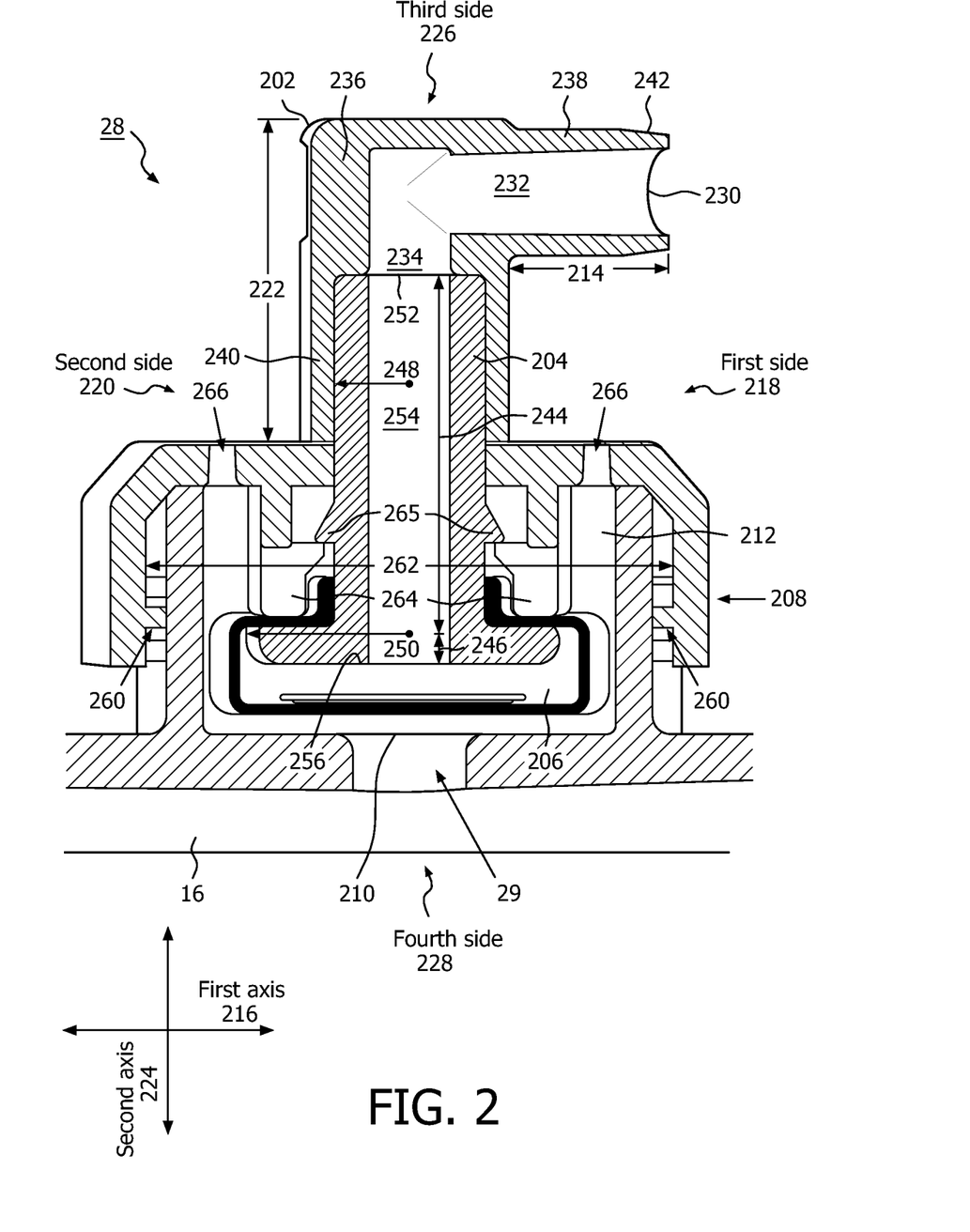
FIG. 2 is a sectional view of a valve in communication with an exhalation port.

FIG. 2 is a sectional view of valve 28 in communication with exhalation port 29. Valve 28 comprises pressurization control line inlet 202, column 204, chamber 206, housing cap 208, and/or other components. Exhalation port 29 comprises orifice 210, chamber 212, and/or other components.

In some embodiments, pressurization control line inlet 202 is generally "L" (or elbow) shaped, with a first length 214 running along a first axis 216 from a first side 218 to a second side 220, and a second length 222 running along a second axis 224 from a third side 226 toward a fourth side 228. In some embodiments, pressurization control line inlet 202 comprises a first orifice 230, a flow path 232, a second orifice 234, and an elbow housing 236.

Elbow housing 236 comprises a first pipe 238, corresponding in length and direction to first length 214, joined to a second pipe 240, corresponding in length and direction to second length 222. First pipe 238 comprises a tapered end 242 of the outside diameter of the pipe running from first side 218 (narrower) toward second side 220 (wider). In some embodiments, a tube shaped pressurization control line may couple to elbow housing 236 by slipping over tapered end 242. Toward and end of elbow housing 236 opposite tapered end 242, the inside diameter of second pipe 240 is configured to slip over column 204. In some embodiments, the cross sectional shape of first pipe 238 and/or second pipe 240 may be a shape other than circular.

Pressurization control line inlet 202 receives a control flow of gas from a pressure source through first orifice 230 on first side 218 of elbow housing 236. In some embodiments, first orifice 230 may be generally circular shaped. From first orifice 230, flow path 232 runs through elbow housing 236 along first axis 216 toward second side 220 of elbow housing 236 that is opposite first side 218. In some embodiments, flow path 232 may be generally cylindrically shaped, for example. In some embodiments, some or all of flow path 232 may have a cross section other than circular. Toward an end of flow path 232 opposite first orifice 230, flow path 232 experiences a bend toward fourth side 228. At the end of flow path 232 opposite first orifice 230, flow path 232 forms second orifice 234 in pressure control line inlet 202. In some embodiments, second orifice 234 may be generally circular shaped.

In some embodiments, column 204 is located toward fourth side 228 from pressurization control line inlet 202, along second axis 224. In some embodiments, column 204 may be generally cylindrically shaped, for example, with a first length 244, a second length 246, a first radius 248, and a second radius 250. In some embodiments, some or all of column 204 may have a cross-sectional shape other than circular.

Column 204 houses orifice 252, flow path 254, and orifice 256. Orifice 252 communicates with second orifice 234 in elbow housing 236 of pressurization control line inlet 202. In some embodiments, orifice 252 may be generally circular shaped. From orifice 252, flow path 254 runs through column 204 along second axis 224 toward fourth side 228 of column 204 and terminates in orifice 256. In some embodiments, flow path 254 may be generally cylindrically shaped, for example. In some embodiments, orifice 256 may be generally circular shaped. In some embodiments, orifice 252, some or all of flow path 254, and/or orifice 256 may have a cross section other than circular.

Orifice 256 communicates with chamber 206. Chamber 206 comprises a hollow area in communication with orifice 256, toward fourth side 228 of valve 28. The walls of chamber 206 are joined to column 204 such that no gas escapes from chamber 206. The walls of chamber 206 are formed from a flexible material such that the volume of chamber 206 expands when pressurized by the control flow of gas and contracts when the pressure of the control flow of gas is reduced and/or stopped. The control flow of gas may be generated by a pressure generator, communicated to valve 28 via a pressurization control line, and/or controlled with a processor as described above with respect to FIG. 1. The volume of chamber 206 decreases when the processor controls the pressure generator to decrease the pressure of the control flow of gas to valve 28 (described with respect to FIG. 1). In some embodiments, the walls of chamber 206 may be made from a flexible material such as, for example, a low durometer (0 to approximately 40 shore) material, a polymer, a thermoplastic polymer, an elastic material, and/or other materials.

Orifice 210 of exhalation port 29 communicates with subject interface 16 located toward fourth side 228 on second axis 224, and chamber 212 of exhalation port 29 toward third side 226 on second axis 224. In some embodiments, orifice 210 may be generally circular shaped. In some embodiments, chamber 212 may be generally cylindrically shaped. In some embodiments, orifice 210 and/or chamber 212 may have a cross section other than circular.

Column 204 and chamber 206 are positioned inside chamber 212 with chamber 206 toward fourth side 228 along second axis 224 such that when the volume of chamber 206 expands with pressurization from the control flow of gas, orifice 210 may be substantially sealed by chamber 206. Flow through orifice 210 may resume when the processor controls the pressure generator to decrease the pressure of the control flow of gas to valve 28 (described with respect to FIG. 1), allowing chamber 206 to contract and unseal orifice 210.

Housing cap 208 is configured to close an open end of chamber 212 toward third side 226 of chamber 212. Housing cap 208 is configured to close the open end of chamber 212 by threading to chamber 212 at threads 260. The present disclosure contemplates that methods other than threading may be used to join housing cap 208 to chamber 212. Valve 28 may be adapted to fit various subject interfaces by attaching via various different joining methods. The cross section of housing cap 208 is generally semicircular shaped with the open side of the semicircle facing fourth side 228. The inner diameter 262 of housing cap 208 may range from about 0.6 inches to about 0.8 inches and is large enough to fit over and thread to the outside diameter of chamber 212, and/or other subject interfaces. In some embodiments, the inner diameter 262 of housing cap 208 is controlled by the maximum diameter of one or more housing cap orifices 266 and/or the maximum diameter of chamber 206. Housing cap 208 is configured such that column 204 passes through housing cap 208. An annular tab 265 of column 204 is configured to seat against seat 264. Housing cap 208 and column 204 are configured such that no gas escapes from chamber 212 through an area between housing cap 208 and column 204. The general shapes and approximate dimensions described herein with respect to housing cap 208 are not intended to be limiting. Housing cap 208 may comprise other shapes and/or dimensions that allow it to function as described in the present disclosure. For example, dimensional changes to subject interface 16 may result in dimensional changes to housing cap 208 and/or other features of valve 28.

One or more housing cap orifices 266 communicate with chamber 212 on fourth side 228 of housing cap 208 and communicate with the ambient environment on third side 226 of housing cap 208. Valve 28 is configured such that gas may be exhaled from subject interface 16 through exhalation port 29 when chamber 206 does not seal orifice 210. The exhaled gas then flows out to the ambient environment through orifice(s) 266. In some embodiments, housing cap orifices 266 are open (not occluded) and/or movement of chamber 206 is unrestricted during inflation and/or deflation of chamber 206.

Figure 3:
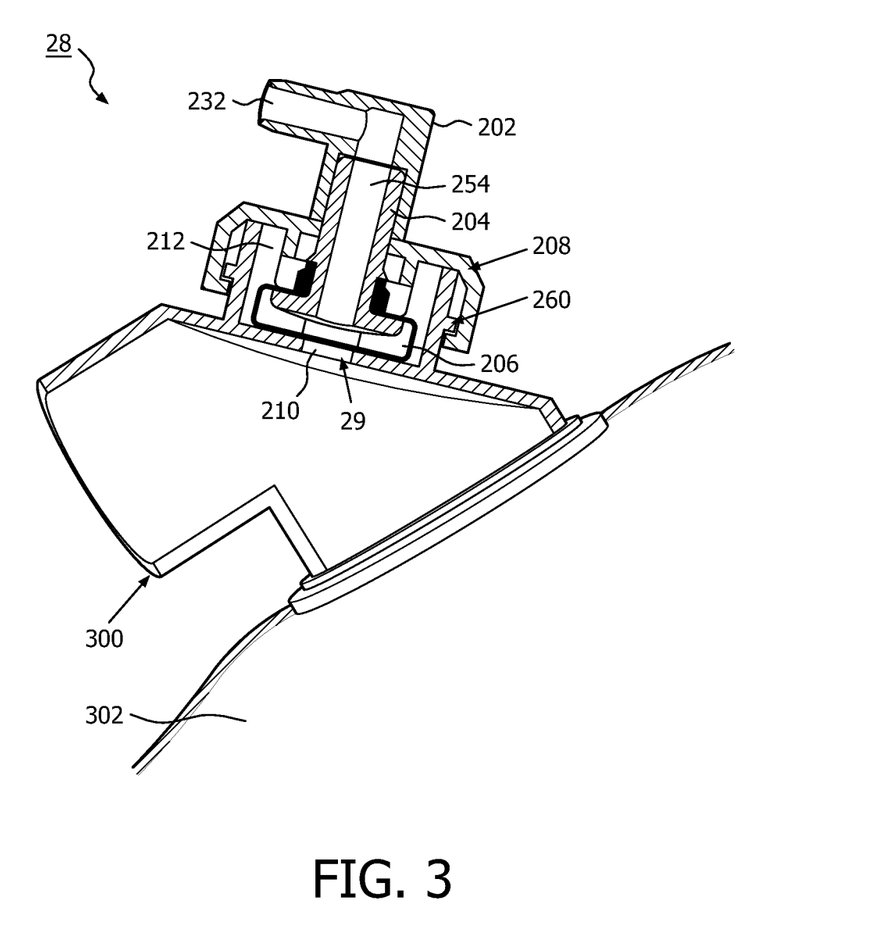
FIG. 3 depicts another sectional view of the valve and shows a cross sectional view of an elbow flow component.

FIG. 3 depicts another cross sectional view of valve 28 and also shows a cross sectional view of an elbow flow component 300. FIG. 3 shows valve 28 mounted to elbow flow component 300, and elbow flow component 300 mounted to a portion of a mask 302. In some embodiments, elbow flow component 300 is a standard component used in mask manufacture. Elbow flow component 300 may be configured to replace the elbow flow component of many interface appliance (e.g., mask) variants. In some embodiments, elbow flow component 300 may be an aftermarket accessory configured to adapt valve 28 to an existing interface appliance (e.g., mask), and/or other components of a subject interface. When the volume of chamber 206 expands with pressurization from a control flow of gas, orifice 210 may be substantially sealed by chamber 206, reducing and/or stopping flow from elbow flow component 300 through exhalation port 29. Flow from elbow flow component 300 through orifice 210 of exhalation port 29 may resume when the processor controls the pressure generator to decrease the pressure of the control flow of gas to valve 28 (described with respect to FIG. 1), allowing chamber 206 to contract and unseal orifice 210.

Figure 4:
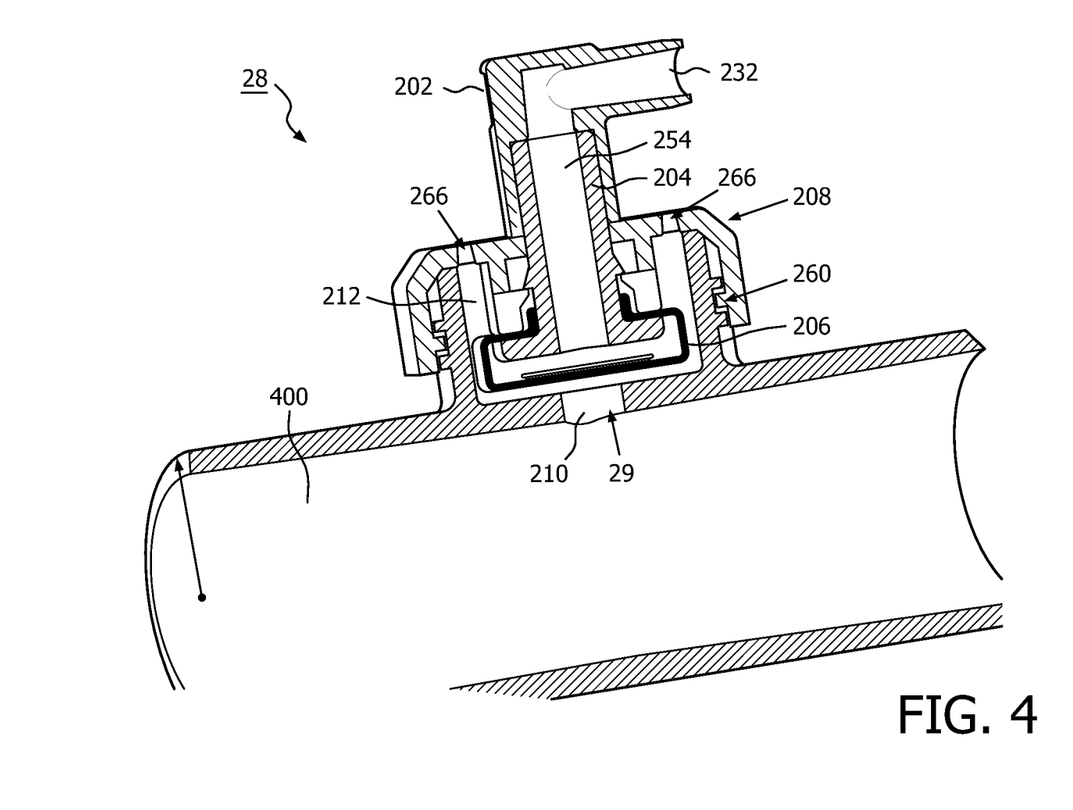
FIG. 4 shows the valve incorporated into a modular flow component.

FIG. 4 shows valve 28 incorporated into a modular flow component 400. Modular flow component 400 has a radius 402 such that modular flow component 402 may be removably incorporated into one or more standard subject interfaces. Modular flow component 400 may be incorporated into a subject interface (e.g., subject interface 16 from FIG. 1) in-line with a conduit (e.g., conduit 24 shown in FIG. 1), an interface appliance (e.g., interface appliance 26 shown in FIG. 1), and/or other components (e.g., elbow flow component 300 shown in FIG. 3). In some embodiments, valve 28 and modular flow component 400 may be incorporated in a subject interface between the conduit and the interface appliance, as close to the interface appliance as possible, to minimize the fixed dead-space of the respiratory circuit. In some embodiments, valve 28 may be incorporated directly into a conduit (e.g., conduit 24 shown in FIG. 1) of a subject interface (e.g., subject interface 16 shown in FIG. 1). As shown in FIG. 4, when the volume of chamber 206 expands with pressurization from a control flow of gas, orifice 210 may be substantially sealed by chamber 206, reducing and/or stopping flow from modular flow component 400 through exhalation port 29. Flow from modular flow component 400 through orifice 210 of exhalation port 29 may resume when the processor controls the pressure generator to decrease the pressure of the control flow of gas to valve 28 (described with respect to FIG. 1), allowing chamber 206 to contract and unseal orifice 210.

In some embodiments, valve 28 may be attached directly to an interface appliance, such as an OptiLife mask, and/or other interface designed for carbon dioxide rebreathing. In some embodiments, valve 28 may be included in a kit configured such that a doctor, patient, and/or other user may deploy valve 28 in an off-the-shelf standard interface appliance, and/or conduit. The kit may include, for example, a port cutter, an adapter configured to mount valve 28 to the interface appliance, a conduit, and/or elbow flow component, a leak port seal to eliminate leak through the leak port (part of a standard mask), and/or other components.

Figure 5:
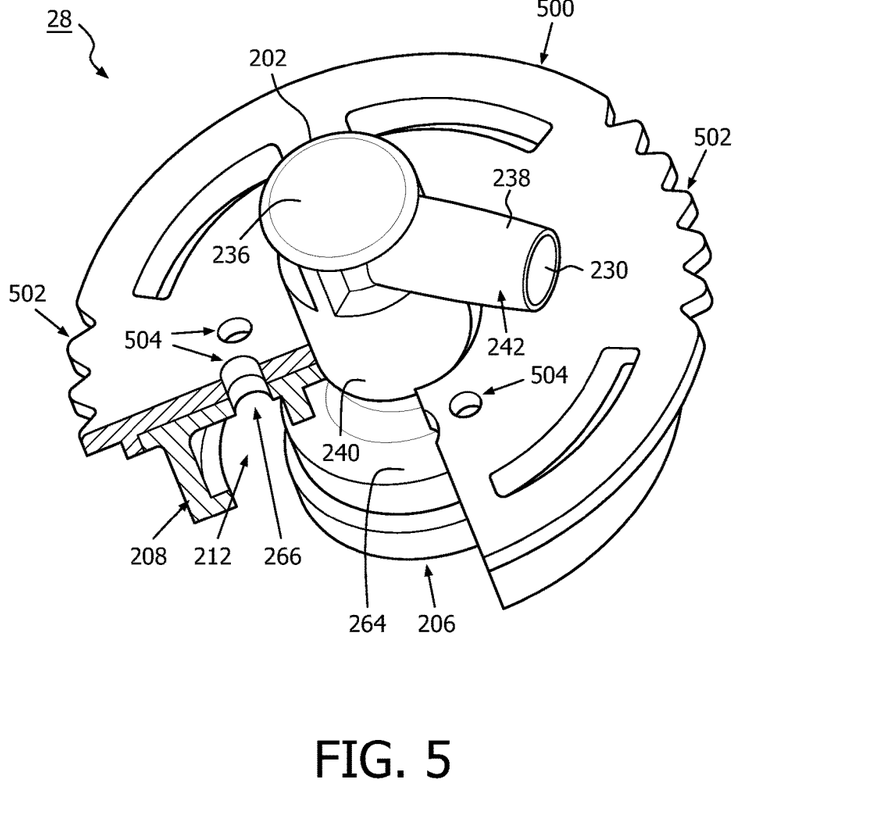
FIG. 5 is a view of the valve that includes a variable leak adjustment disk.

FIG. 5 is a view of valve 28 that includes a variable leak adjustment disk 500. In some embodiments, valve 28 may include a variable leak adjustment disk 500 configured to control gas leakage from subject interface 16 through valve 28. Variable leak adjustment disk 500 comprises one or more grip points 502, one or more leak orifices 504, and/or other components. Variable leak adjustment disk 500 is configured to engage housing cap 208 on the side of housing cap 208 that is opposite chamber 212. Variable leak adjustment disk 500 is configured such that a user may manually rotate variable leak adjustment disk 500 relative to housing cap 208 to align and/or partially align one or more variable leak orifices 504 with one or more housing cap orifices 266 to manually control the amount of gas leaked from valve 28. The degree to which the one or more leak orifices 504 are aligned to the one or more housing cap orifices 266 controls the amount of leak through valve 28. Alignment of the leak orifices 504 to the housing cap orifices 266 results in maximum leak through valve 28. When leak orifices 504 are not aligned to housing cap orifices 266 such that no part of any leak orifice 504 overlaps any part of any housing cap orifices 266, manual leak adjustment disk 500 forms a seal with housing cap 208 such that substantially no gas is leaked through valve 28. In some embodiments, valve 28 combined with leak adjustment disk 500 may be configured to allow an increased flow rate through valve 28 relative to the flow rate through valve 28 alone (as described in FIG. 1-4). In some embodiments, valve 28 combined with leak adjustment disk 500 may be configured to allow a decreased flow rate through valve 28 relative to the flow rate through valve 28 alone (as described in FIG. 1-4).

Figure 6:
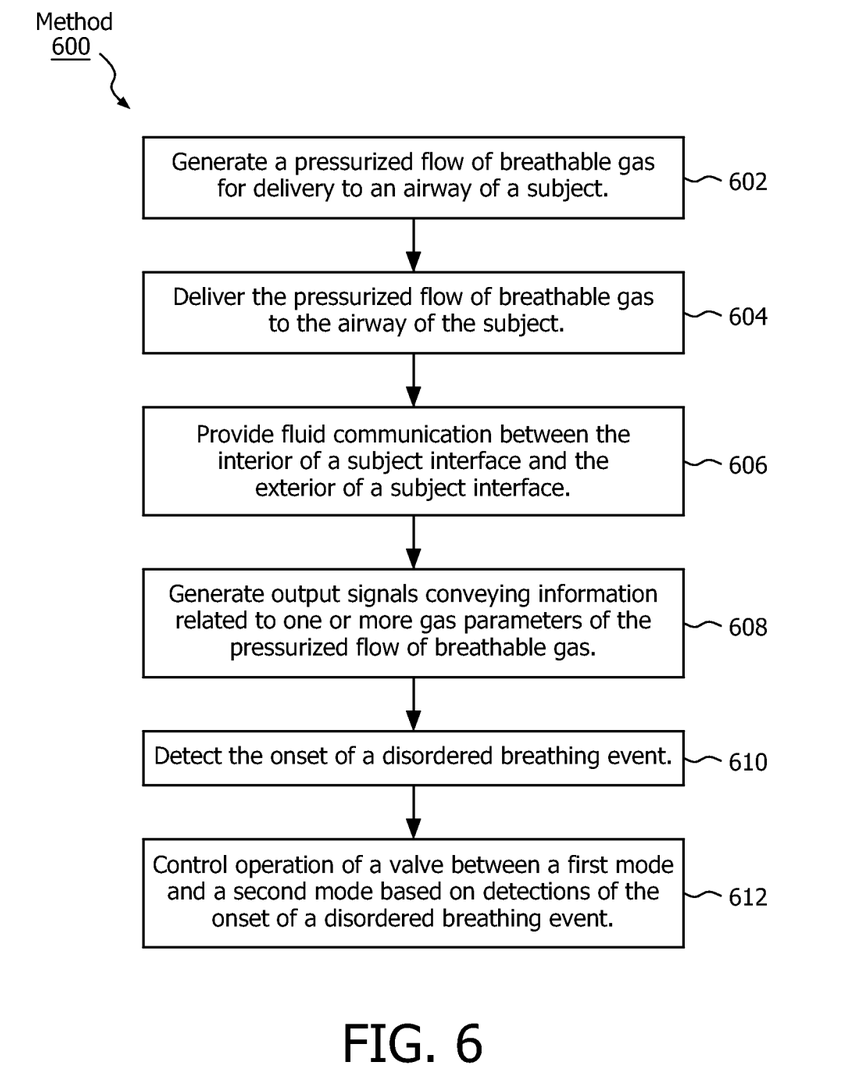
FIG. 6 illustrates a method to control gas flow during exhalation of a subject.

FIG. 6 illustrates a method 600 to control gas flow during exhalation of a subject. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, a pressurized flow of breathable gas is generated for delivery to an airway of a subject. In some embodiments, operation 602 is performed by a pressure generator the same as or similar to pressure generator 14 (shown in FIG. 1 and described herein).

At an operation 604, the pressurized flow of breathable gas is delivered to the airway of the subject with a subject interface. In some embodiments, operation 604 is performed by a subject interface the same as or similar to subject interface 16 (shown in FIG. 1 and described herein).

At an operation 606, fluid communication is provided between the interior of the subject interface and the exterior of the subject interface with and exhalation port. In some embodiments, operation 606 is performed by an exhalation port the same as or similar to exhalation port 29 (shown in FIG. 1 and described herein).

At an operation 608, output signals conveying information related to one or more gas parameters of the pressurized flow of breathable gas are generated. In some embodiments, operation 608 is performed by sensors the same as or similar to sensors 18 (shown in FIG. 1, and described herein).

At an operation 610, the onset of a disordered breathing event is detected. The onset of the disordered breathing event is determined based on the output signals. In some embodiments, operation 610 is performed by a processor module the same as or similar to disordered breathing event detection module 54 (shown in FIG. 1 and described herein).

At an operation 612, flow through the exhalation port is controlled by a valve, wherein such control includes causing the valve to switch between a first mode in which the exhalation port is opened to permit gas flow from the airway of the subject during exhalation, and a second mode in which flow through the exhalation port is restricted with respect to the flow in the first mode, wherein such control comprises switching operation of the valve between the first mode and the second mode based on detections of the onset of disordered breathing events. In some embodiments, operation 612 is performed by a processor module the same as or similar to control module 56 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. An exhalation valve system configured to control gas flow during exhalation of a subject. the system comprising:
   a pressure generator configured to generate a pressurized flow of breathable gas for delivery to an airway of the subject;
   a subject interface comprising a conduit configured to communicate the pressurized flow of breathable gas to the airway of the subject, and an exhalation port configured to place an interior of the subject interface in communication with an exterior of the subject interface,
   a valve, coupled to the exhalation port of the subject interface configured to selectively control flow through the exhalation port, the valve comprising a pressure chamber having flexible walls, the pressure chamber comprising a hollow area in fluid communication with the pressure generator via a pressurization control line that is separate from the conduit,
      wherein gas from the pressure generator conducted to the valve by the pressurization control line causes movement of the flexible walls to change a volume of the pressure chamber but does not escape the pressure chamber through the valve. the exhalation port, or the conduit, the valve operating in a first mode in which the exhalation port is opened to permit gas flow from the airway of the subject during exhalation, and a second mode in which flow through the exhalation port is restricted with respect to the flow in the first mode; and
      wherein the valve is coupled to the pressurization control line at a first end of the valve and coupled to the exhalation port at a second opposite end of the valve, the pressurization control line affecting the volume of the pressure chamber;
   a flow component configured to adapt the valve to the exhalation port, the flow component being configured to removably couple with the exhalation port and the valve to form a flow path between the exhalation port and the valve;
   one or more sensors configured to generate output signals conveying information related to one or more gas parameters of the pressurized flow of breathable gas; and
   one or more processors configured to execute computer program modules, the computer program modules comprising:
      a disordered breathing event detection module configured to detect the onset of a disordered breathing event, wherein the onset of the disordered breathing event is detected based on the output signals of the sensors; and
      a control module configured to control operation of the valve between the first mode and the second mode based on detections by the disordered breathing event detection module, wherein the control module is configured to cause movement of the flexible walls and thereby cause the volume of the pressure chamber to (i) expand such that the valve operates in the second mode or (ii) contract such that the valve operates in the first mode.

2. The system of claim 1, wherein the control module is configured to control operation of the valve between the first mode and the second mode by placing the valve in the second mode responsive to a detection by the disordered breathing event detection module of the onset of a disordered breathing event such that during exhalation substantially no gas is communicated from the airway of the subject through the valve.

3. The system of claim 1, wherein the pressurization control line is coupled to the pressure generator separately from the subject interface, and wherein the valve is controlled to operate in the first mode and the second mode by a control flow of gas generated by the pressure generator.

4. The system of claim 1, wherein the flow component includes one or more of an elbow-shaped tube component or a cylindrical tube component and forms an orifice configured to conduct gas to the valve.

5. The system of claim 1, wherein the valve further comprises an exhalation chamber, wherein the pressure chamber is positioned inside the exhalation chamber, and wherein the pressure chamber is configured to expand and contract to block or expose an orifice in the exhalation chamber to facilitate gas flow through the exhalation chamber but not the pressure chamber.

6. The system of claim 2, wherein the control module is configured to control operation of the valve between the first mode and the second mode by placing the valve in the second mode responsive to a detection by the disordered breathing event detection module of the onset of a disordered breathing event such that during exhalation no gas is communicated from the airway of the subject through the valve.

7. A method of controlling, gas flow during exhalation of a subject, the method being performed by a system that includes a pressure generator, a subject interface, one or more sensors, a flow component, and one or more processors, the method comprising:
  generating, with the pressure generator, a pressurized flow of breathable gas for delivery to an airway of the subject;
  delivering the pressurized flow of breathable gas to the airway of the subject with a conduit of the subject interface;
  providing fluid communication between an interior of the subject interface and an exterior of the subject interface through an exhalation port of the subject interface, the exhalation port positioned between the pressure generator and the airway;
  generating, with the one or more sensors, output signals conveying information related to one or more gas parameters of the pressurized flow of breathable gas;
  detecting, with the one or more processors, the onset of a disordered breathing event, wherein the onset of the disordered breathing event is detected based on the output signals;
  controlling, the one or more processors, flow through the exhalation port with a valve coupled to the exhalation port of the subject interface, the valve comprising a pressure chamber having flexible walls, the pressure chamber comprising a hollow area in fluid communication with the pressure generator via a pressurization control line that is separate from the conduit, wherein gas from the pressure generator conducted to the valve by the pressurization control line causes movement of the flexible walls to change a volume of the pressure chamber but does not escape the pressure chamber through the valve, the exhalation port, or the conduit, wherein such control includes causing the valve to switch between a first mode in which the exhalation port is opened to permit gas flow from the airway of the subject during exhalation, and a second mode in which flow through the exhalation port is restricted with respect to the flow in the first mode, wherein such control comprises switching operation of the valve between the first mode and the second mode based on detections of the onset of disordered breathing events, wherein controlling the flow through the exhalation port comprises causing movement of the flexible walls and thereby causing the volume of the pressure chamber to (i) expand such that the valve operates in the second mode or (ii) contract such that the valve operates in the first mode;
  coupling the valve to the pressure generator with the pressurization control line at a first end of the valve and coupling the valve to the exhalation port at a second opposite end of the valve, the pressurization control line affecting the volume of the pressure chamber; and
  adapting the valve to the exhalation port with the flow component, the flow component configured to removably couple with the exhalation port and the valve to form a flow path between the exhalation port and the valve.

8. The method of claim 7, further comprising controlling operation of the valve between the first mode and the second mode by placing the valve in the second mode responsive to a detection of the onset of a disordered breathing event, by the one or more processors, such that during exhalation substantially no gas is communicated from the airway of the subject through the valve.

9. The method of claim 7, further comprising controlling the valve to operate in the first mode and the second mode with a control flow of gas generated by the pressure generator, wherein the control flow of gas from the pressure generator is controlled by the processor.

10. The method of claim 7, wherein the flow component includes one or more of an elbow-shaped tube component or a cylindrical tube component and forms an orifice configured to conduct gas to the valve.

11. The method of claim 7, wherein the valve further comprises an exhalation chamber, wherein the pressure chamber is positioned inside the exhalation chamber, and wherein the pressure chamber is configured to expand and contract to block or expose an orifice in the exhalation chamber to facilitate gas flow through the exhalation chamber but not the pressure chamber.

12. The method of claim 8, further comprising controlling operation of the valve between the first mode and the second mode by placing the valve in the second mode responsive to a detection of the onset of a disordered breathing event, by the one or more processors, such that during exhalation no gas is communicated from the airway of the subject through the valve.

13. An exhalation valve system configured to control gas flow during exhalation of a subject, the system comprising:
  means for generating a pressurized flow of breathable gas for delivery to an airway of the subject;
  means for delivering the pressurized flow of breathable gas to the airway of the subject;
  means for providing fluid communication between an interior of the means for communicating the pressurized flow of breathable gas to the airway of the subject and an exterior of the means for communicating the pressurized flow of breathable gas to the airway of the subject;
  means for generating output signals conveying information related to one or more vas parameters of the pressurized flow of breathable gas;

means for detecting the onset of a disordered breathing event, wherein the onset of the disordered breathing event is detected based on the output signals;

means for controlling flow through the means for interior/exterior communication with means for selectively controlling flow coupled to the means for interior/exterior communication, the means for selectively controlling flow comprising a pressure chamber having one or more movable walls, the pressure chamber comprising a hollow area in fluid communication with the means for generating the pressurized flow of breathable gas via means for coupling the means for selectively controlling flow to the means for generating that is separate from the means for delivering the pressurized flow of breathable gas to the airway of the subject, wherein gas from the means for generating the pressurized flow of breathable gas conducted to the means for controlling flow through the means for interior/exterior communication through the means for coupling the means for selectively controlling flow to the means for generating causes movement of the flexible walls to change a volume of the pressure chamber but does not escape the pressure chamber through the means for selectively controlling flow, the means for interior/exterior communication, or the means for delivering the pressurized flow of breathable gas to the airway of the subject, wherein such control includes causing the means for selectively controlling flow to switch between a first mode in which the means for interior/exterior communication is opened to permit gas flow from the airway of the subject during exhalation, and a second mode in which flow through the means for interior/exterior communication is restricted with respect to the flow in the first mode, wherein such control comprises switching operation of the means for selectively controlling flow between the first mode and the second mode based on detections of the onset of disordered breathing events, wherein controlling the flow through the exhalation port comprises causing movement of the flexible walls and thereby causing the volume of the pressure chamber to (i) expand such that the valve operates in the second mode or (ii) contract such that the valve operates in the first mode;

means for coupling the means for selectively controlling flow to the means for generating at a first end of the means for selectively controlling flow, and means for coupling the means for selectively controlling flow to the means for providing fluid communication between an interior and an exterior of the means for communicating the pressurized flow of breathable gas to the airway of the subject at a second opposite end of the means for selectively controlling flow, the means for coupling the means for selectively controlling flow to the means for generating at a first end of the means for selectively controlling flow affecting the volume of the pressure chamber; and means for adapting the means for selectively controlling flow to the means for interior/exterior communication, the means for adapting configured to removably couple with the means for interior/exterior communication and the means for selectively controlling flow to form a flow path between the means for interior/exterior communication and the means for selectively controlling flow.

14. The system of claim 13, wherein the means for controlling operation of the means for selectively controlling flow between the first mode and the second mode places the means for selectively controlling flow in the second mode responsive to a detection of the onset of a disordered breathing event such that during exhalation substantially no gas is communicated from the airway of the subject through the means for selectively controlling flow.

15. The system of claim 13, wherein the means for controlling controls the means for selectively controlling flow to operate in the first mode and the second mode with a control flow of gas generated by the means for generating.

16. The system of claim 13, wherein the means for adapting includes one or more of an elbow-shaped tube component or a cylindrical tube component and forms an orifice configured to conduct gas to the valve.

17. The system of claim 13, wherein the means for selectively controlling flow further comprises an exhalation chamber, wherein the pressure chamber is positioned inside the exhalation chamber, and wherein the pressure chamber is configured to expand and contract to block or expose an orifice in the exhalation chamber to facilitate gas flow through the exhalation chamber but not the pressure chamber.

18. The system of claim 14, wherein the means for controlling operation of the means for selectively controlling flow between the first mode and the second mode places the means for selectively controlling flow in the second mode responsive to a detection of the onset of a disordered breathing event such that during exhalation no gas is communicated from the airway of the subject through the means for selectively controlling flow.

19. An exhalation valve system configured to control gas flow during exhalation of a subject, the system comprising:
  a pressure generator configured to generate a pressurized flow of breathable gas for delivery to an airway of the subject;
  a subject interface comprising a conduit configured to communicate the pressurized flow of breathable gas to the airway of the subject, and an exhalation port configured to place an interior of the subject interface in communication with an exterior of the subject interface;
  a valve, coupled to the exhalation port of the subject interface configured to selectively control flow through the exhalation port, the valve comprising a pressure chamber having flexible walls, the pressure chamber comprising a hollow area in fluid communication with the pressure generator via a pressurization control line that is separate from the conduit,
    wherein gas from the pressure generator conducted to the valve by the pressurization control line causes movement of the flexible walls to change a volume of the pressure chamber but does not escape the pressure chamber through the valve, the exhalation port, or the conduit, the valve operating in a first mode in which the exhalation port is opened to permit gas flow from the airway of the subject during exhalation, and a second mode in which flow through the exhalation port is restricted with respect to the flow in the first mode; and
    wherein the valve further comprises a variable leak adjustment disk configured to control gas leakage from the subject interface via one or more leak orifices formed in the leak adjustment disk, the one or more leak orifices configured to be aligned with corresponding orifices in a housing of the valve;
  a flow component configured to adapt the valve to the exhalation port, the flow component being configured to removably couple with the exhalation port and the valve to form a flow path between the exhalation port and the valve;

one or more sensors configured to generate output signals conveying information related to one or more gas parameters of the pressurized flow of breathable gas; and one or more processors configured to execute computer program modules, the computer program modules comprising:

a disordered breathing event detection module configured to detect the onset of a disordered breathing event, wherein the onset of the disordered breathing event is detected based on the output signals of the sensors; and a control module configured to control operation of the valve between the first mode and the second mode based on detections by the disordered breathing event detection module, wherein the control module is configured to cause movement of the flexible walls and thereby cause the volume of the pressure chamber to (i) expand such that the valve operates in the second mode or (ii) contract such that the valve operates in the first mode.

20. A method of controlling gas flow during exhalation of a subject, the method being performed by a system that includes a pressure generator, a subject interface, one or more sensors, a flow component, and one or more processors, the method comprising:

generating, with the pressure generator, a pressurized flow of breathable gas for delivery to an airway of the subject;

delivering the pressurized flow of breathable gas to the airway of the subject with a conduit of the subject interface;

providing fluid communication between an interior of the subject interface and an exterior of the subject interface through an exhalation port of the subject interface, the exhalation port positioned between the pressure generator and the airway;

generating, with the one or more sensors, output signals conveying information related to one or more gas parameters of the pressurized flow of breathable gas;

detecting, with the one or more processors, the onset of a disordered breathing event, wherein the onset of the disordered breathing event is detected based on the output signals;

controlling, by the one or more processors, flow through the exhalation port with a valve coupled to the exhalation port of the subject interface, the valve comprising, a pressure chamber having flexible walls, the pressure chamber comprising a hollow area in fluid communication with the pressure generator via a pressurization control line that is separate from the conduit, wherein gas from the pressure generator conducted to the valve by the pressurization control line causes movement of the flexible walls to change a volume of the pressure chamber but does not escape the pressure chamber through the valve, the exhalation port, or the conduit, wherein such control includes causing the valve to switch between a first mode in which the exhalation port is opened to permit gas flow from the airway of the subject during exhalation, and a second mode in which flow through the exhalation port is restricted with respect to the flow in the first mode, wherein such control comprises switching operation of the valve between the first mode and the second mode based on detections of the onset of disordered breathing events, wherein controlling the flow through the exhalation port comprises causing movement of the flexible walls and thereby causing the volume of the pressure chamber to (i) expand such that the valve operates in the second mode or (ii) contract such that the valve operates in the first mode;

controlling leak from the subject interface with a variable leak adjustment disk of the valve, the variable leak adjustment disk configured to control gas leakage from the subject interface via one or more leak orifices formed in the leak adjustment disk, the one or more leak orifices configured to be aligned with corresponding orifices in a housing of the valve; and adapting the valve to the exhalation port with the flow component, the flow component configured to removably couple with the exhalation port and the valve to form a flow path between the exhalation port and the valve.

21. An exhalation valve system configured to control gas flow during exhalation of a subject, the system comprising:

means for generating a pressurized flow of breathable gas for delivery to an airway of the subject;

means for delivering the pressurized flow of breathable s to the airway of the subject;

means for providing fluid communication between an interior of the means for communicating the pressurized flow of breathable gas to the airway of the subject and an exterior of the means for communicating the pressurized flow of breathable gas to the airway of the subject;

means for generating output signals conveying information related to one or more gas parameters of the pressurized flow of breathable gas;

means for detecting the onset of a disordered breathing event, wherein the onset of the disordered breathing event is detected based on the output signals;

means for controlling flow through the means for interior/exterior communication with means for selectively controlling flow coupled to the means for interior/exterior communication,. the means for selectively controlling flow comprising a pressure chamber having one or more movable walls, the pressure chamber comprising a hollow area in fluid communication with the means for generating the pressurized flow of breathable gas via means for coupling the means for selectively controlling flow to the means for generating that is separate from the means for delivering the pressurized flow of breathable gas to the airway of the subject, wherein gas from the means for generating the pressurized flow of breathable gas conducted to the means for controlling flow through the means for interior/exterior communication through the means for coupling the means for selectively controlling flow to the means for generating causes movement of the flexible walls to change a volume of the pressure chamber but does not escape the pressure chamber through the means for selectively controlling flow, the means for interior/exterior communication, or the means for delivering the pressurized flow of breathable gas to the airway of the subject, wherein such control includes causing the means for selectively controlling flow to switch between a first mode in which the means for interior/exterior communication is opened to permit gas flow from the airway of the subject during exhalation, and a second mode in which flow through the means for interior/exterior communication is restricted with respect to the flow in the first mode, wherein such control comprises switching operation of the means for selectively controlling flow between the first mode and the second mode based on detections of the onset of disordered breathing events, wherein controlling the flow through the exhalation port comprises causing movement of the flexible walls and thereby causing the volume of the pressure chamber to (i) expand such that the valve operates in the second mode or GO contract such that the valve operates in the first mode; and means for adapting the means for selectively controlling, flow to the means for interior,/exterior communication, the means for adapting configured to removably couple with the means for interior/exterior communication and the means for selectively controlling flow to form a flow path between the means for interior/exterior communication and the means for selectively controlling flow;

wherein the means for selectively controlling flow further comprises a variable leak adjustment disk configured to control gas leakage from the means for interior/exterior communication via one or more leak orifices formed in the leak adjustment disk, the one or more leak orifices configured to be aligned with corresponding orifices in a housing of the means for selectively controlling flow.

* * * * *